United States Patent
Soultanidis et al.

(10) Patent No.: US 10,131,588 B2
(45) Date of Patent: *Nov. 20, 2018

(54) PRODUCTION OF C2+ OLEFINS

(71) Applicant: ExxonMobil Chemical Patents Inc., Baytown, TX (US)

(72) Inventors: Nikolaos Soultanidis, Houston, TX (US); James H. Beech, Jr., Kingwood, TX (US); Steven E. Silverberg, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/543,271

(22) Filed: Nov. 17, 2014

(65) Prior Publication Data

US 2015/0158785 A1    Jun. 11, 2015

Related U.S. Application Data

(60) Provisional application No. 61/912,866, filed on Dec. 6, 2013.

(30) Foreign Application Priority Data

Feb. 5, 2014    (EP) .................................... 14153943

(51) Int. Cl.
    *C07C 1/20*    (2006.01)

(52) U.S. Cl.
    CPC ............ *C07C 1/20* (2013.01); *C07C 2521/04* (2013.01); *C07C 2523/80* (2013.01); *C07C 2529/40* (2013.01); *Y02P 30/42* (2015.11)

(58) Field of Classification Search
    CPC ....................................................... C07C 1/20
    USPC ................................................. 585/329, 640
    See application file for complete search history.

(56) References Cited

U.S. PATENT DOCUMENTS

| | | | |
|---|---|---|---|
| 3,700,585 A | 10/1972 | Chen et al. |
| 3,702,886 A | 11/1972 | Argauer et al. |
| 3,709,979 A | 1/1973 | Chu et al. |
| 3,832,449 A | 8/1974 | Rosinski et al. |
| 3,911,041 A | 10/1975 | Kaeding et al. |
| 3,928,483 A | 12/1975 | Chang et al. |
| 3,931,349 A | 1/1976 | Kuo |
| 4,016,218 A | 4/1977 | Haag et al. |
| 4,016,245 A | 4/1977 | Plank et al. |
| 4,046,825 A | 9/1977 | Owen et al. |
| 4,049,573 A | 9/1977 | Kaeding |
| 4,062,905 A | 12/1977 | Chang et al. |
| 4,076,842 A | 2/1978 | Plank et al. |
| 4,079,095 A | 3/1978 | Givens et al. |
| 4,079,096 A | 3/1978 | Givens et al. |
| 4,088,706 A | 5/1978 | Kaeding |
| 4,111,847 A | 9/1978 | Stiles |
| 4,138,440 A | 2/1979 | Chang et al. |
| RE29,948 E | 3/1979 | Dwyer et al. |
| 4,229,424 A | 10/1980 | Kokotailo |
| 4,234,231 A | 11/1980 | Yan |
| 4,439,409 A | 3/1984 | Puppe et al. |
| 4,440,871 A | 4/1984 | Lok et al. |
| 4,499,327 A | 2/1985 | Kaiser |
| 4,556,477 A | 12/1985 | Dwyer |
| 4,826,667 A | 5/1989 | Zones et al. |
| 4,873,067 A | 10/1989 | Valyocsik et al. |
| 4,954,325 A | 9/1990 | Rubin et al. |
| 5,236,575 A | 8/1993 | Bennett et al. |
| 5,250,277 A | 10/1993 | Kresge et al. |
| 5,336,825 A | 8/1994 | Choudhary et al. |
| 5,362,697 A | 11/1994 | Fung et al. |
| 5,370,851 A | 12/1994 | Wilson |
| 5,633,417 A | 5/1997 | Beck et al. |
| 5,675,047 A | 10/1997 | Beck et al. |
| 5,936,135 A | 8/1999 | Choudhary et al. |
| 6,077,498 A | 6/2000 | Cabanas et al. |
| 6,200,536 B1 | 3/2001 | Tonkovich et al. |
| 6,219,973 B1 | 4/2001 | Lafferty |
| 6,365,792 B1 | 4/2002 | Stapf et al. |
| 6,518,475 B2 | 2/2003 | Fung et al. |
| 6,756,030 B1 | 6/2004 | Rohde et al. |
| 7,014,807 B2 | 3/2006 | O'Brien |
| 7,015,369 B2 | 3/2006 | Hack et al. |
| 7,022,888 B2 | 4/2006 | Choudhary et al. |

(Continued)

FOREIGN PATENT DOCUMENTS

| CN | 101244969 | 8/2008 |
|---|---|---|
| EP | 0293032 | 7/1993 |

(Continued)

OTHER PUBLICATIONS

Goto, D.; Harada, Y.; Furumoto, Y.; Takahashi, A.; Fujitani, T.; Oumi, Y.; Sadakane, M.; Sano, T. "Conversion of ethanol to propylene over HZSM-5 type zeolites containing alkaline earth metals"; Appl. Cat. A. (2010), 383, pp. 89-95.*
Steinar Kvisle et al. "methanol-to Hydrocarbons" In: "handbook of Heterogeneous Catalysis, Part 12. Inorganic Reactions", Mar. 15, 2008, Wiley-VCH Verlag GmbH & Co. vol. 13, pp. 2950-2965.
Chemical and Engineering News, 63(5), 27 (1985).
Chemistry Letters, 35 (2), 142-147, 2006.
Catalysis Letters, 28, 241-248 (1994).
G. Centi, G. Cum, J.L.G. Fierro and J. M. Lopez Nieto, "Direct Conversion of Methane, Ethane, and Carbon Dioxide to Fuels and Chemicals", The Catalyst Group Resources Inc., Spring House, 2008.

(Continued)

*Primary Examiner* — Renee Robinson
*Assistant Examiner* — Aaron W Pierpont

(57) ABSTRACT

Carbon monoxide and molecular hydrogen are converted to an alcohol mixture, which is separated into a first methanol-containing stream and a second $C_{2+}$ alcohol-containing stream. The first stream's methanol is converted into a propylene-rich product, and the second stream's $C_{2+}$ alcohol is converted to ethylene and additional propylene.

20 Claims, No Drawings

(56) References Cited

U.S. PATENT DOCUMENTS

| | | | |
|---|---|---|---|
| 7,371,915 B1* | 5/2008 | Kalnes | C07C 1/20 585/638 |
| 7,453,018 B2 | 11/2008 | Dakka et al. | |
| 7,799,962 B2 | 9/2010 | Dakka et al. | |
| 7,977,519 B2 | 7/2011 | Iaccino et al. | |
| 8,119,076 B2 | 2/2012 | Keusenkothen et al. | |
| 8,138,384 B2 | 3/2012 | Iaccino et al. | |
| 8,552,247 B2 | 10/2013 | Noe et al. | |
| 2005/0107481 A1* | 5/2005 | Janssen | C07C 1/20 518/726 |
| 2005/0107651 A1* | 5/2005 | Sher | C07C 1/20 585/639 |
| 2006/0149109 A1* | 7/2006 | Ruziska | C07C 1/24 585/639 |
| 2007/0161717 A1 | 7/2007 | Hu et al. | |
| 2007/0259972 A1 | 11/2007 | Lattner et al. | |
| 2008/0033218 A1 | 2/2008 | Lattner et al. | |
| 2012/0083637 A1 | 4/2012 | Clem et al. | |
| 2012/0330080 A1* | 12/2012 | Liu | B01J 29/48 585/640 |

FOREIGN PATENT DOCUMENTS

| | | |
|---|---|---|
| EP | 1704132 | 7/2005 |
| EP | 2184269 | 5/2010 |
| GB | 2191212 | 12/1987 |
| WO | 97/17290 | 5/1997 |
| WO | 2004/087624 | 10/2004 |
| WO | 2012/099674 | 7/2012 |

OTHER PUBLICATIONS

R.M. Navarro, M.A. Pena and J.L.G.Fierro, Chem. Rev., vol. 107, p. 3952, 2007.
V.R. Choudhary, A.K.Kinage and T.V.Choudhary, Science, vol. 275, pp. 1286-1288, 1997.
V.R. Choudhary and P. Devadas, Microporous and Mesoporous Materials, vol. 23, pp. 231-238, 1998.
J. Guo, H. Lou, H. Zhao, L.Zheng and X.Zheng, Journal of Molecular Catalysis A: Chemical, vol. 239, pp. 222-227, 2005.
J. Gou, H. Lou and X. Zheng, Journal of Natural Gas Chemistry, vol. 18, pp. 260-272, 2009.
O.A. Anunziata, G. A. Eimer and L.B.Pierella, Applied Catalysis A: General, vol. 190, pp. 169-176, 2000.
Alkhawaldeh Ammar et al.: "Conversion of mixtures of methane and ethylene or acetylene into liquids", Pre-Print Archive— Amer. Inst. of Chem Engr., Spring National Meeting, New Orleans, LA USA, Mar. 11-14, 2001 Proceedings of the Second Topical Conference on Natural Gas Utilization, American Institute of Chemical Engineer, Jan. 1, 2002 (Jan. 1, 2002) p. 416 paragraph 3; figure 4.
X1Ao-Song Li et al; "A process for a high yield of aromatics from the oxygen-free conversion of methane: combining plasma with Ni/HZSM-5 catalysts", Green Chemistry, vol. 9, No. 6, Jan. 1, 2007 (Jan. 1, 2007), p. 647, col. 2, last paragraph p. 650, col. 2, paragraph 1: figures 1-3.
V Ha: "Aromatization of methane over zeolite supported molybdenum: active sites and reaction mechanism", Journal of Molecular Catalysis A: Chemical, vol. 181, No. 1-2, Mar. 25, 2002, pp. 283-290.
Oscar A. Anunziata: Catalysis Letters, vol. 87, No. 3/4, Jan. 1, 2003, 167-171.
"Conversion of biomass-derived syngas to alcohols and C2 oxygenates using supported Rh catalysts in a microchannel reactor", Jiami Hu, Yong Wang, Chusha Cao, Douglas C. Elliot, Don J. Stevens, James F. White, 1, Jan. 30, 2007, Catalysis Today vol. 120, pp. 90-95.
H. Yagita et al., Environmental Catalysis, G. Centi et al. Eds. SCI Publicaiton, Rome, 1995, pp. 639-642.
"Iron Particle Size Effects for Direct Production of Lower Olefins for Synthesis Gas", Hirsa M. Torres Galvis, Johannes H. Bitter, Thomas Davidian, Matthijs Ruitenbeek, A. Iulian Dugulan, and Krijn P. de Jong.s.1 : Journal of American Chemical Society, Sep. 6, 2012, Journal of the American Chemical Society.
"Supported Iron Nanoparticles as Catalysts for Sustainable Production of Lower Olefins", Hirsa M. Torres Galvis, Johannes H. Bitter, Chaitanya B. Khare, Matthijs Ruitenbeak, A. Luian Dugulan, and Krijn P. de Jong, 335, Feb. 17, 2012, Science, vol. 6070, pp. 835-838.
"Heterogeneous Catalytic Synthesis of Ethanol from Biomass-Derived Syngas", James J. Spivey, Adefemi Egbebi, Mar. 7, 2007, Chemical Society Reviews, vol. 38, pp. 1514-15.
"Ruthenium Melt Catalysis", Producing Chemicals from Synthetic Gas, Knifton, John F. 2, Austin, Texas s.n., 1985, vol. 29, p. 63.
Choudhary et al., Angew. Chem. Int. Ed. 2005, 44, 4381-4385.
J.R. Aderson, Appl. Catal. 47, (1989) 177.
J.S. Lee et al, Catal. Rev-Sci. Eng., 30 (1988) 249.
G.J. Hutchings et al., Chem Soc.Rev., 18 (1989) 25.
Science 153 (1966) 1393 "High Temperature Synthesis of Aromatics Hydrocarbons from Methane".
J.H. Lunsford, Ang Chem. Intl. Ed. Engl. 24 (1995), 970.
J. Haggin, Methane to Gasoline Plant Adds to New Zealand Liquid Fuel Resources, Chemical & Engineering News p. 22, Jun. 22, 1987.
J.H. Lunsford, The Catalytic Conversion of Methane to Higher Hydrocarbons, Catal. Today, vol. 6, p. 235, 1990.
Synthesis gas conversion utilizing mixed catalyst composed of CO reducing catalyst and solid acid: II. Direct syntheseis of aromatic hydrocarbons from synthesis gas. Kaoru Fujimoto, Yoshihiro Kudo, Hiro-o Tominaga. May 1984, Journal of Catalysis, vol. 87, is. 1. 136-143.
Selective Conversion of Methanol into Aromatic Hydrocarbons Over Silver Exchanged ZAM-5 Zeolites. Inoue, Yoshihiro, Nakashiro, Katsumi, Ono, Yoshio. S.L.: Elsevier; 1995, Microporous Materials, vol. 4, 379-383.
Sachchit Majhi et al. "Direct conversion of methane with methanol toward higher hydrocarbon over GA modified Mo/H-ZSM-5 catalyst", Journal of Industrial and Engineering Chemistry, vol. 20, No. 4, Oct. 14, 2013, pp. 2364-2369.
Anunziata O.A. et al: "Methane transformation into aromatic hydrocarbons by activiation with LPG over Zn-ZSM-11 Zeolite" Catalysis Letters, Springer New York LLC, United States, vol. 58, No. 4, Apr. 1, 1999, pp. 235-239.
Zhang, C-L et al: "Aromatization of Methane in the absence of oxygen over mo-based catalysts supported on different types of zeolites", Catalysis Letters, vol. 56, No. 4, Jan. 1, 1999, 207-213.
Parisa Moghimpour Bijani et al: "nonoxidative Aromatization of CH 4 using C3H8 as a Coreactant: Thermodynamic and Experimental Analysis", Industrial and Engineering Chemistry Research, vol. 53, No. 2, Jan. 15, 2014, pp. 572-581.

* cited by examiner

PRODUCTION OF C2+ OLEFINS

CROSS-REFERENCE TO RELATED APPLICATIONS

This application claims priority to U.S. Patent Application Ser. No. 61/912,866, filed Dec. 6, 2013, the disclosure of which is incorporated herein by reference in its entirety. This application also claims priority to European Patent Application No. 14153943.7, filed Feb. 5, 2014. Cross reference is made to the following related patent applications: (i) U.S. patent application Ser. No. 14/543,243, filed Nov. 17, 2014; (ii) P.C.T. Patent Application No. PCT/US2014/065947, filed Nov. 17, 2014; (iii) P.C.T. Patent Application No. PCT/US2014/065956, filed Nov. 17, 2014; (iv) U.S. patent application Ser. No. 14/543,365, filed Nov. 17, 2014; (v) U.S. patent application Ser. No. 14/543,426, filed Nov. 17, 2014; (vi) P.C.T. Patent Application No. PCT/US2014/065969, filed Nov. 17, 2014; (vii); U.S. patent application Ser. No. 14/543,405, filed Nov. 17, 2014(viii) and P.C.T. Patent Application No. PCT/US2014/065961, filed Nov. 17, 2014.

FIELD

This disclosure relates to processes for producing $C_{2+}$ olefins, equipment and materials useful in such processes, and to the use of such olefins in, for example, the production of polymers.

BACKGROUND

Although methane is abundant, its relative inertness has limited its utility in conversion processes for producing higher-value hydrocarbons. For example, oxidative coupling methods generally involve highly exothermic and potentially hazardous methane combustion reactions, and frequently require expensive oxygen generation facilities and produce large quantities of environmentally sensitive carbon oxides. Non-oxidative methane conversion is equilibrium-limited, and temperatures ≥about 800° C. are needed for methane conversions greater than a few percent.

One way to avoid this difficulty involves converting methane to a mixture comprising carbon monoxide and molecular hydrogen (the mixture being conventionally referred to as "syngas"), converting the syngas to a mixture of oxygenates, and then converting the oxygenates to olefins. See, e.g., U.S. Patent Application Publications Nos. 2005/0107481 A1, 2008/0033218 A1, and 2007/0259972 A1, which disclose aspects of converting syngas to a mixture comprising $C_1$ alcohol and $C_2$ alcohol, and then converting the mixture to a product mixture comprising ethylene and propylene. According to those references, approximately 100% of the mixture's ethanol is selectively converted to ethylene. The mixture's methanol, in contrast, produces (i) ethylene and propylene, in approximately equal amounts, and (ii) a significant amount of by-products. The by-products can include, e.g., one or more of molecular hydrogen, water, alcohols, carboxylic acids, ethers, carbon oxides, ammonia and other nitrogenated compounds, arsines, phosphines, and chlorides. The by-products can also include hydrocarbons, such as one or more of $C_4$ to $C_{30}$ olefins, acetylene, methyl acetylene, propadiene, butadiene, butyne, and the like, and combinations thereof.

A more flexible process is desired, which can produce ethylene and propylene over a wide range of relative amounts. In order to increase the efficiency of ethylene and propylene recovery from the product mixture, a process is desired which produces fewer by-products than does the conventional process. Advantageously, by-products (if any) should include (i) molecules which can be efficiently separated from the product mixture's ethylene and propylene, such as water, and (ii) relatively high-value hydrocarbon such as $C_{5+}$ hydrocarbon.

SUMMARY

Certain aspects of the invention are directed toward producing $C_{2+}$ olefin, such as ethylene and propylene, from an alcohol-containing mixture. The alcohol-containing mixture can comprise, e.g., ≥2 wt. % methanol and ≥1 wt. % ethanol, and can have a molar ratio of methanol to $C_{2+}$ alcohol in the range of from 1.5:1 to 3:1. At least first and second streams are separated from the alcohol-containing mixture. The first stream comprises at least a portion of alcohol-containing mixture's methanol. The second stream comprises at least a portion of the alcohol-containing mixture's $C_{2+}$ alcohol.

At least a portion of the first stream's methanol is reacted to produce a first hydrocarbon and a first oxygenate. The first hydrocarbon and first oxygenate can be conducted away from the reaction as components of a first product mixture. The first product mixture can further comprise, e.g., unreacted components of the first stream, by-products of the reacting, etc. The first hydrocarbon, which is produced by reacting the first stream's methanol, comprises ≥25.0 wt. % of propylene and ≤10.0 wt. % of ethylene, the weight percents being based on the weight of the first hydrocarbon. At least a portion of the second stream's $C_{2+}$ alcohol is reacted to produce a second hydrocarbon and a second oxygenate. The second hydrocarbon and second oxygenate can be conducted away from the reaction as components of a second product mixture. The second product mixture can further comprise, e.g., unreacted components of the second stream, by-products of the reacting, etc. The hydrocarbon produced by reacting the second stream's $C_{2+}$ alcohol comprises ethylene and propylene, the total amount of ethylene+propylene being ≥10.0 wt. % based on the weight of hydrocarbon produced by reacting the second stream's $C_{2+}$ alcohol.

The alcohol-containing mixture can be produced from a feed mixture comprising molecular hydrogen and carbon monoxide, such as syngas. The syngas can be produced from hydrocarbon, such as methane, or other suitable carbon source, such as coal or biomass. The syngas can comprise, e.g., molecular hydrogen and ≥5.0 wt. % of carbon monoxide, based on the weight of the syngas, and the syngas can have an $H_2$: $(CO+CO_2)$ molar ratio in the range of from 0.5 to 20, e.g., an $H_2$:CO ratio in the range of from 0.5 to 20. The syngas is then reacted to produce the alcohol-containing mixture (this aspect of the process being referred to as alcohol synthesis). The alcohol synthesis can further comprise recycling carbon monoxide and/or molecular hydrogen from the alcohol-containing mixture to the feed mixture.

Certain aspects of the invention are based on the discovery that it is more efficient to separate the methanol from the $C_{2+}$ alcohols upstream of alcohol conversion, rather than convert the alcohol-containing mixture and then separate the various products and by-products. More particularly, it has been found that separately processing the methanol and $C_{2+}$ alcohol results in a significant increase in the olefin product's propylene:ethylene weight ratio over that of the conventional process. For example, when the alcohol-containing mixture has a molar ratio of methanol to $C_{2+}$ alcohol in the range of from 1.5:1 to 3:1, the olefin product's propylene:ethylene weight ratio can be ≥1.0, e.g., ≥1.5. Moreover, it is observed that separately processing the specified alcohol-containing mixture's methanol and $C_{2+}$ alcohol leads to a significant decrease in the amount of by-products, with remaining by-products, if any, being either of relatively high value and/or easy to separate from the desired ethylene and propylene products. The process is flexible, and can be operated to produce propylene and ethylene over a wider propylene:ethylene weight ratio range than can conventional processes.

In other aspects, the invention relates to a process for producing ethylene and propylene from a carbon-containing source material, e.g., natural gas or components thereof, such as methane. The process includes reacting at least a portion of the source material's hydrocarbon to produce a feed mixture, the feed mixture comprising molecular hydrogen and ≥5.0 wt. % of carbon monoxide, based on the weight of the feed mixture, the feed mixture having an $H_2$:(CO+ $CO_2$) molar ratio in the range of from 0.5 to 20. The process continues by reacting at least a portion of the feed mixture's molecular hydrogen with at least a portion of the feed mixture's carbon monoxide, the reacting being carried out in the presence of a catalyst comprising one or more elements or oxides thereof from Groups 8 to 12 of the Periodic Table, to produce an alcohol-containing mixture, the alcohol-containing mixture comprising methanol and ≥2 wt. % of one or more $C_{2+}$ alcohols, based on the weight of the alcohol-containing mixture. The alcohol-containing mixture has, e.g., a molar ratio of methanol to $C_{2+}$ alcohol in the range of from 1.5 to 3. First and second streams are separated from the alcohol-containing mixture, wherein (i) the first stream comprises ≥50.0 wt. % of the alcohol-containing mixture's methanol based on the weight of the intermediate product's methanol, and (ii) the second stream comprises ≥50.0 wt. % of the alcohol-containing mixture's $C_{2+}$ alcohols, based on the weight of the alcohol-containing mixture's $C_{2+}$ alcohols. At least part of the first stream's methanol is reacted in a first stage to produce a first hydrocarbon and first oxygenate, wherein (i) the first hydrocarbon comprises $C_{3-}$ olefin and (ii) the $C_{3-}$ olefin comprises ≥25.0 wt. % of propylene and ≤10.0 wt. % of ethylene, based on the weight of the first hydrocarbon's $C_{3-}$ olefin. At least part of the second stream's $C_{2+}$ alcohol is reacted in a second stage to produce a second hydrocarbon and a second oxygenate, wherein (i) the second hydrocarbon comprises $C_{2+}$ olefin and (ii) the $C_{2+}$ olefin comprises a total amount of ethylene+propylene that is ≥10.0 wt. %, based on the weight of the second hydrocarbon's $C_{2+}$ olefin.

DETAILED DESCRIPTION

Definitions

For the purpose of this description and appended claims, the following terms are defined. The term "$C_n$" hydrocarbon wherein n is a positive integer, e.g., 1, 2, 3, 4, or 5, means a hydrocarbon having n number of carbon atom(s) per molecule. The term "$C_{n+}$" hydrocarbon wherein n is a positive integer, e.g., 1, 2, 3, 4, or 5, means a hydrocarbon having at least n number of carbon atom(s) per molecule. The term "$C_{n-}$" hydrocarbon wherein n is a positive integer, e.g., 1, 2, 3, 4, or 5, means a hydrocarbon having no more than n number of carbon atom(s) per molecule. The term "hydrocarbon" encompasses mixtures of hydrocarbon having different values of n. The term "alcohol-containing mixture" means a mixture comprising $C_1$ alcohol and $C_2$ alcohol, and optionally other species including, e.g., $C_{3+}$ alcohol and/or non-alcohols. As used herein, the numbering scheme for the groups of the Periodic Table of the Elements is as disclosed in Chemical and Engineering News, 63(5), 27 (1985).

Certain aspects of the invention relate to producing $C_{2+}$ olefin, particularly ethylene and propylene, from alcohol-containing mixtures. Optionally, the alcohol-containing mixture is produced by reacting a mixture comprising molecular hydrogen and carbon monoxide (a "feed mixture-"or"feed stream"), such as syngas. Optionally, the feed mixture is obtained by reacting hydrocarbon (a "source material"), the source material comprising, e.g., $C_{1+}$ hydrocarbon, such as methane and/or ethane.

Methanol and ethanol are separated from the alcohol-containing mixture and processed separately. Certain aspects of the invention utilize alcohol-containing mixtures comprising a mixture of $C_{3-}$ alcohol. The $C_{3-}$ alcohol mixture is subsequently separated into a first, methanol-containing stream and a second, $C_2$-$C_3$ alcohol-containing stream. The methanol in the first stream can then be converted into a propylene-rich product while the $C_2$ and $C_3$ alcohol in the second stream can be dehydrated to ethylene and additional propylene. These aspects are described in more detail below. The invention is not limited to these aspects, and this description is not meant to foreclose other embodiments within the broader scope of the invention.

Alcohol-Containing Mixture

In certain aspects, the alcohol-containing mixture comprises ≥2 wt. % of methanol and ≥1 wt. % of $C_{2+}$ alcohol, the weight percents being based on the weight of the alcohol-containing mixture. For example, the alcohol-containing mixture can comprise at least 15 wt. % methanol and at least 7.5 wt. % ethanol, based on the weight of the alcohol-containing mixture. Optionally, the alcohol-containing mixture comprises ≥15 wt. % of methanol and ≥7.5 wt. % of ethanol and/or propanol.

Optionally, the alcohol-containing mixture product contains methanol in an amount ranging from about 2 wt. % to about 99 wt. %, based on the weight of the alcohol-containing mixture, and contains an amount of ethanol and/or propanol effective for separation into the specified first and second streams. For example, the alcohol-containing mixture can comprise 1 wt. % to 75 wt. % methanol, e.g., 5 wt. % to 60 wt. % methanol, such as 10 wt. % to 50 wt. % methanol, based on the weight of the alcohol-containing mixture. The alcohol-containing mixture can comprise, e.g., an amount of ethanol and/or propanol that is ≥1 wt. %, e.g., ≥2 wt. %, such as ≥6 wt. %, or ≥10 wt. %, based on the weight of the alcohol-containing mixture. For example, the alcohol-containing mixture can comprise ≥2 wt. % of $C_2$ and/or $C_3$ alcohol, e.g., ≥10 wt. %, such as ≥15 wt. %, or ≥20 wt. %, based on the weight of the alcohol-containing mixture. In certain aspects, the alcohol-containing mixture comprises ≥15 wt. % methanol and ≥7.5 wt. % $C_2$ and/or $C_3$ alcohol, e.g., 15 wt. % to 50 wt. % methanol and 7.5 wt. % to 25 wt. % $C_2$ and/or $C_3$ alcohol.

In certain aspects, the alcohol-containing mixture comprises ≥0.1 wt. % of $C_3$ alcohols, based on the weight of the alcohol-containing mixture, e.g., ≥0.5 wt. %, such as ≥1.0 wt. %. In certain aspects, the alcohol-containing mixture comprises ≥0.1 wt. % water, e.g., ≥1.0 wt. % water, based on the weight of the alcohol-containing mixture. For example, the amount of water in the alcohol-containing mixture can be in the range of from 0.1 wt. % water to 20 wt. % water, such as from 1 wt. % water to 10 wt. % water. Optionally, the second stream comprises ≥0.1 wt. % water, e.g., ≥1.0 wt. % water, based on the weight of the second stream. For example, the amount of water in the second stream can be in the range of from 0.1 wt. % water to 20 wt. % water, such as from 1 wt. % water to 10 wt. % water.

In certain aspects, the alcohol-containing mixture comprises ≤1.0 mole % of carbon monoxide, e.g., ≤0.1 mole %, such as ≤0.01 mole %; ≤1.0 mole % of carbon dioxide, e.g., ≤0.1 mole %, such as ≤0.01 mole %; ≤1.0 mole % of aldehyde, e.g., ≤0.1 mole %, such as ≤0.01 mole %; and ≤1.0 mole % of molecular hydrogen, e.g., ≤0.1 mole %, such as ≤0.01 mole %; the mole percents being per mole of the alcohol-containing mixture.

Conventional means can be utilized for separating the specified first and second streams from the alcohol-containing mixture. The first stream generally comprises ≥10.0 wt. % of the alcohol-containing mixture's methanol based on the weight of the intermediate product's methanol. The second stream generally comprises ≥10.0 wt. % of the alcohol-containing mixture's $C_{2+}$ alcohols, based on the weight of the alcohol-containing mixture's $C_{2+}$ alcohols.

In certain aspects, the first stream comprises ≥10.0 wt. % of the alcohol-containing mixture's methanol, based on the weight of methanol in the alcohol-containing mixture, e.g., ≥50.0 wt. %, such as ≥75.0 wt. %, or ≥90.0 wt. %, or ≥95.0 wt. %, or ≥99.0 wt. % of the alcohol-containing mixture's methanol. In certain aspects of the invention, the first stream comprises ≥50.0 wt. % methanol, e.g., ≥75.0 wt. %, such as ≥90.0 wt. %, or ≥99.0 wt. % methanol, based on the weight of the first stream. Although it can be undesirable to do so, for reasons including inefficiency and cost, it is not necessary to obtain all of the first stream's methanol via methanol removal from the alcohol-containing mixture. For example, methanol can be added to the first stream when insufficient methanol is obtained from the alcohol-containing mixture, as might occur when the alcohol-containing mixture contains less than the desired amount of methanol or when inefficient separation means are utilized for transferring methanol from the alcohol-containing mixture to the first stream. In certain aspects, ≥50.0 wt. % of the first stream's methanol is methanol removed from the alcohol-containing mixture, e.g., ≥75.0 wt. %, such as ≥90.0 wt. %, or ≥99.0 wt. %, based on the weight of the first stream's methanol. In related aspects, substantially all of the first stream's methanol is obtained from the alcohol-containing mixture. Although $C_{2+}$ alcohol (and other non-methanol oxygenates) can be present in the first stream, it is preferred that the amounts of these species do not exceed 1.0 wt. %, based on the weight of the first stream, e.g., ≤0.1 wt. %, such as ≤0.01 wt. %. Water can be present in the first stream, but it is preferred that the amounts of water does not exceed 10.0 wt. %, based on the weight of the first stream, e.g., ≤1 wt. %, such as ≤0.1 wt. %. Generally, the first stream does not contain a significant amount of hydrocarbon, whether saturated or otherwise. For example, the amount of hydrocarbon in the first stream is generally ≤1.0 wt. %, based on the weight of the first stream, e.g., ≤0.1 wt. %, such as ≤0.01 wt. %.

In certain aspects, the second stream comprises ≥10.0 wt. % of the alcohol-containing mixture's $C_{2+}$ alcohol, based on the weight of $C_{2+}$ alcohol in the alcohol-containing mixture, e.g., ≥50.0 wt. %, such as ≥75.0 wt. %, or ≥90.0 wt. %, or ≥95.0 wt. %, or ≥99.0 wt. % of the alcohol-containing mixture's $C_{2+}$ alcohol. In certain aspects of the invention, the second stream comprises ≥50.0 wt. % $C_{2+}$ alcohol, e.g., ≥75.0 wt. %, such as ≥90.0 wt. %, or ≥99.0 wt. % $C_{2+}$ alcohol, based on the weight of the second stream. Optionally, the second stream's $C_{2+}$ alcohol comprises ≥60.0 wt. % ethanol, such as ≥80.0 wt. % ethanol, based on the weight of the second stream's $C_{2+}$ alcohol. Optionally, the second stream's $C_{2+}$ alcohol comprises ≥0.5 wt. % propanol, e.g., ≥1.0 wt. %, such as ≥5.0 wt. %, based on the weight of the second stream's $C_{2+}$ alcohol. Optionally, the second stream has a propanol:ethanol weight ratio in the range of from about 0.01 to 1.0, e.g., 0.05 to 0.70, such as about 0.10 to about 0.50. Although it can be undesirable to do so, for reasons including inefficiency and cost, it is not necessary to obtain all of the second stream's $C_{2+}$ alcohol (or individual alcohol components thereof) via $C_{2+}$ alcohol removal from the alcohol-containing mixture. For example, $C_{2+}$ alcohol can be added to the second stream when insufficient methanol is obtained from the alcohol-containing mixture, as might occur when the alcohol-containing mixture contains less than the desired amount of $C_{2+}$ alcohol, or when inefficient separation means are utilized for transferring $C_{2+}$ alcohol from the alcohol-containing mixture to the second stream. In certain aspects, ≥50.0 wt. % of the second stream's $C_{2+}$ alcohol is $C_{2+}$ alcohol removed from the alcohol-containing mixture, e.g., ≥75.0 wt. %, such as ≥90.0 wt. %, or ≥99.0 wt. %, based on the weight of the second stream's $C_{2+}$ alcohol. In related aspects, substantially all of the second stream's $C_{2+}$ alcohol is obtained from the alcohol-containing mixture. Although methanol (and other non-$C_{2+}$ alcohol oxygenates, such as $CO_2$) can be present in the second stream, it is preferred that the amounts of these species do not exceed 1.0 wt. %, based on the weight of the second stream, e.g., ≤0.1 wt. %, such as ≤0.01 wt. %. Water can be present in the second stream, but it is preferred that the amount of water does not exceed 20.0 wt. %, based on the weight of the second stream, e.g., ≤10 wt. %, such as ≤1.0 wt. %, or ≤0.1 wt. %.

Generally, the second stream does not contain a significant amount of hydrocarbon, whether saturated or otherwise. For example, the amount of hydrocarbon in the second stream is generally ≤1.0 wt. %, based on the weight of the second stream, e.g., ≤0.1 wt. %, such as ≤0.01 wt. %.

Aspect relating to producing a carbon monoxide—molecular hydrogen mixture such as syngas by reacting a carbon-containing source material will now be described in more detail. The invention is not limited to these aspects, and this description is not meant to foreclose other embodiments within the broader scope of the invention.

Producing a Carbon Monoxide—Molecular Hydrogen Mixture

In certain aspects, methane and/or other carbon-containing source material is converted via a mixture of carbon monoxide and molecular hydrogen, e.g., syngas. The carbon monoxide—molecular hydrogen mixture is reacted to produce a mixture of lower alcohols, the lower alcohols being divided into separate methanol and $C_{2+}$ alcohol streams before the alcohol streams are converted to olefins.

The type of carbon-containing source material used is not critical. The source material can comprise, e.g., methane and other lower ($C_{4-}$) alkanes, such as contained in a natural gas stream, or heavier hydrocarbonaceous materials, such as coal and biomass. Desirably, the source material comprises ≥10 vol. %, such as ≥50 vol. %, based on the volume of the source material, of at least one hydrocarbon, especially methane.

The source material can be initially converted to a carbon monoxide—molecular hydrogen mixture by any convenient method, including those well-established in the art. Suitable methods include those described in U.S. Patent Application Publications Nos. 2007/0259972 A1, 2008/0033218 A1, and 2005/0107481, each of which is incorporated by reference herein in its entirety. Certain aspects where the carbon monoxide—molecular hydrogen mixture is syngas will now be described in more detail. The invention is not limited to these aspects, and this description is not meant to foreclose other aspects within the broader scope of the invention, such as those where the carbon monoxide—molecular hydrogen mixture does not contain syngas. a3

Natural gas can be converted to syngas by steam reforming. The first step normally involves the removal of inert components in the natural gas, such as nitrogen, argon, and carbon dioxide. Natural gas liquids will also be recovered and directed to other processing or transport. The treated natural gas will comprise primarily methane and some ethane with small amounts of higher alkanes, such as propane. Preferably, the natural gas comprises more than 90 vol. % methane. The treated natural gas is then contacted with steam in the presence of a catalyst, such as one or more metals or compounds thereof selected from Groups 7 to 10 of the Periodic Table of the Elements supported on an attrition resistant refractory support, such as alumina. The contacting is normally conducted at high temperature, such as in the range of from 800° C. to 1100° C., and pressures <5000 kPa. Under these conditions, methane converts to carbon monoxide and hydrogen according to reactions, such as:

$$CH_4 + H_2O \leftrightarrow CO + 3H_2.$$

Steam reforming is energy intensive in that the process consumes over 200 kJ/mole of methane consumed. A second method is partial oxidation, in which the methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

$$CH_4 + \tfrac{3}{2}O_2 \leftrightarrow CO + 2H_2O \qquad (i),$$

$$CO + H_2O \leftrightarrow CO_2 + H_2 \qquad (ii).$$

Partial oxidation is exothermic and yields a significant amount of heat. Because one reaction is endothermic and the other is exothermic, steam reforming and partial oxidation are often performed together for efficient energy usage. Combining the steam reforming and partial oxidation yields a third process wherein the heat generated by the partial oxidation is used to drive the steam reforming to yield syngas.

Syngas can be utilized as a feed mixture to the alcohol-synthesis reaction. The syngas can be reacted by any convenient methods, including conventional methods such as those disclosed in U.S. Patent Application Publications Nos. 2007/0259972 A1, 2008/0033218 A1, and 2005/0107481. Aspects of the invention which include reacting at least a portion of the syngas in the presence of at least one alcohol-synthesis catalyst to produce the specified alcohol-containing mixture, will now be described in more detail. The invention is not limited to these aspects, and this description is not meant to foreclose other aspects within the broader scope of the invention, including aspects utilizing non-catalytic methods and those utilizing a different catalyst.

Producing an Alcohol-Containing Mixture

Syngas can be utilized as a carbon monoxide—molecular hydrogen mixture for synthesizing $C_{2+}$ olefin. In certain aspects, the invention relates to a process including the catalytic conversion of at least part of the syngas to a mixture of methanol and $C_{2+}$ alcohol, especially ethanol and propanol. The choice of alcohol-synthesis catalyst is not critical. Conventional alcohol-synthesis catalysts can be used in the process, such as one or more elements or oxides from Groups 8 to 12 of the Periodic Table, for example Ni, Cu, Zn, Mn, Ru, Rh, Ag and combinations thereof. Optionally, the alcohol-synthesis catalyst is supported on a refractory support, such as one or more of alumina, zirconia, titania, calcia silica, and magnesia. The catalyst can be promoted by doping with one or more elements or compounds thereof from Groups 1 or 2 of the Periodic Table, such as Cs, K, and Ca. Desirably, the catalyst comprises copper oxide and zinc oxide, for example in an atomic ratio of copper to zinc from 1:1 to 8:1. An example of such a catalyst is disclosed in U.S. Pat. No 4,111,847, the entire contents of which are incorporated herein by reference. One advantage of such mixed copper and zinc oxide catalysts is that they exhibit a combination of a high selectivity for the conversion of syngas to alcohols and a low selectivity for the conversion of syngas back to methane. In one embodiment, the catalyst comprises a mixed copper and zinc oxide catalyst promoted with an alkali metal, such as caesium, and supported on alumina. An example of such a catalyst is disclosed in U.S. Patent Publication No 2007/0161717, the entire contents of which are incorporated herein by reference.

The syngas conversion process can be conducted over a wide range of conditions, e.g., a temperature in the range of from 200° C. to 350° C., a pressure in the range of from 300 psia to 1200 psia (2068 to 8274 kPa), a gas hourly space velocity (vol/vol) of 1000 hr$^{-1}$ to 6000 hr$^{-1}$, and a $H_2$/CO molar ratio of $\geq 0.5$, e.g., in the range of from 0.5:1 to 4:1, or from 0.5:1 to 3:1. Desirably the reaction is conducted in a reactor that allows high heat transfer rates so as to reduce the formation of by-products, such as methane and carbon dioxide. A suitable reactor is a microchannel reactor which includes a plurality of microchannel reaction channels in thermal contact with a plurality of adjacent heat exchange microchannels. In such a reactor each microchannel may have a width of 5 mm or less, with the reactor having 10, 100, 1000 or more channels. Non-limiting examples of microchannel reactors are disclosed in U.S. Pat. Nos. 6,200, 536 and 6,219,973 (both of which are incorporated by reference herein in their entirety).

By controlling the catalyst and reaction conditions as described above, the syngas conversion process can be operated to produce a mixture of methanol and $C_{2+}$ alcohols, in which methanol comprises at least 40 wt. % of the total conversion products, $C_{2+}$ alcohols comprise at least 20 wt.% of the total conversion products and the ratio of methanol to $C_{2+}$ alcohols in the product effluent is in the range of from 1.5 to 3. Typical rates of conversion of the syngas that can be achieved during the process are from 10 to 50 mole %. A representative reaction occurring during the syngas conversion process is as follows:

$$4CO + 8H_2 \rightarrow 2CH_3OH + C_2H_5OH + H_2O.$$

Any unreacted syngas, and any by-products of the syngas conversion, can readily be removed from process effluent. Optionally, at least a portion of any separated syngas and/or at least a portion of any components thereof, are recycled to a location upstream of the alcohol-synthesis reaction, e.g., for combining with the syngas feed to the alcohol-synthesis reaction. This can be accomplished in one or more separation stages located downstream of the syngas conversion, which will now be described in more detail.

In certain aspects, a first separation stage is utilized for separating from the alcohol-containing mixture one or more of (i) the first stream, (ii) the second stream, (iii) an aqueous stream, (iv) unreacted syngas and components thereof, and (v) additional streams such as additional by-product streams. The first separation stage can include one or more separation means, e.g., membrane means, sorption means, fractional distillation means, knock-out drum means, extraction means, etc. Conventional separations means are suitable, such as those described in U.S. Patent Application Publication No. 2008/0033218 A1, but the invention is not limited thereto.

In certain aspects, at least a portion of any unreacted syngas is optionally separated from the alcohol-containing mixture and recycled to the conversion process (the alcohol-synthesis reaction). The separation can be carried out in the specified first separation stage. Although at least a portion of any carbon dioxide and/or water present in the syngas or produced in the alcohol-synthesis reaction can be recycled, e.g., for regulating the alcohol-synthesis reaction, it is within the scope of the invention to utilize the first separation stage for removing at least portions of these from the process.

In certain aspects, the process effluent obtained from the alcohol-synthesis reaction comprises (or consists essentially of, or consists of) $C_{3-}$ alcohols, carbon monoxide, molecular hydrogen, and optionally water and/or carbon dioxide. The first separation stage can be utilized at least for separating and conducting away (for storage, recycle, or further processing) ≥90.0%, ≥95.0%, such as ≥99.0% of each (weight basis) of the carbon monoxide, molecular hydrogen, and optionally water and/or carbon dioxide in the process effluent. The remainder of the process effluent from the alcohol-synthesis reaction constitutes the alcohol-containing mixture. The alcohol-containing mixture comprises mainly of $C_{3-}$ alcohols, e.g., ≥50.0 wt. % $C_{3-}$ alcohols, e.g., ≥75.0 wt. %, such as ≥99.0 wt. %, based on the weight of the alcohol-containing mixture. In certain aspects, the alcohol-containing mixture comprises least 15 wt. % methanol and at least 7.5 wt. % ethanol, based on the weight of the alcohol-containing mixture. Further separations, which can be carried out by fractional distillation in the specified first separation stage, can be utilized for separating from the alcohol-containing mixture (i) a methanol-containing first stream (methanol has a normal boiling point of 64.7° C.) and (ii) a $C_{2+}$ alcohol-containing second stream (ethanol has a normal boiling point of 78.4° C.). These streams are then separately converted to olefinic products, with the methanol in the first stream being converted into a propylene-rich product while the $C_2$-$C_3$ alcohols in the second stream are dehydrated to ethylene and additional propylene.

Surprisingly, it has been found to be more efficient to separate the methanol from the $C_2$-$C_3$ alcohols upstream of alcohol conversion process, rather than convert the entire $C_{3-}$ alcohol mixture and then separate the various products and by-products, particularly when increased amounts of propylene are desired. It has also been surprisingly found that the process produces fewer undesirable by-products than oxygenate-to-olefin processes. The conventional oxygenate-to-olefins process described in U.S. Patent Application Publication No. 2007/0259972, discloses that approximately 100% of ethanol in its methanol-ethanol feed is converted to ethylene, which strongly suggests that the many by-products enumerated in that patent application are produced by methanol conversion. Surprisingly, it has been found that separating and converting at least a portion of the alcohol-containing mixture's methanol produces fewer by-products than does converting all of the methanol in the second stage in the presence of $C_{2+}$ alcohol. Certain by-products are particularly undesired because, e.g., they have a deleterious effect on the process, are difficult to separate from the desired light olefin products, etc. Such undesired by-products include one or more of alcohols; carboxylic acids; ethers, carbon oxides; ammonia and other nitrogenated compounds; arsine; phosphine; chlorides; molecular hydrogen; hydrocarbons containing one or more carbon-carbon triple bonds, such as acetylene; and hydrocarbons containing two or more carbon-carbon double bonds, propadiene and butadiene. The amount of such by-products in the first and second product mixtures (on a weight basis, based on the combined weight of the first and second product mixtures) is generally ≤0.9 times that observed in the effluent of an oxygenate-to-olefin reaction utilizing the same alcohol-containing mixture as a feed an operated under substantially the same conditions as those specified for converting the second stream in the second stage of the process, ≤0.75 times, such as ≤0.5 times.

Certain aspects for reacting the first and second streams will now be described in more detail. The invention is not limited to these aspects, and this description is not meant to foreclose other aspects within the broader scope of the invention.

Reacting the First Stream

Conversion of the methanol-containing first stream into a propylene-rich product is conveniently effected by a two-stage process, the first stage being utilized for reacting the first stream's methanol and the second stage being utilized for reacting the second stream's $C_2$-$C_3$ alcohols.

At least a portion of the methanol in the first stream is reacted in a first stage to convert at least a portion of the first stream's methanol to olefins, e.g., $C_{3-}$ olefin, wherein the $C_{3-}$ olefin comprises ≥25.0 wt. % of propylene and ≤10.0 wt. % of ethylene, based on the weight of the $C_{3-}$ olefin. For example, ≥50.0 wt. % of the first stream's methanol, based on the weight of the first stream's methanol, ≥75.0 wt. %, such as ≥90.0 wt. %, or ≥95.0 wt. % can be reacted in the first stage to produce a first hydrocarbon and a first oxygenate. Generally, (i) the first hydrocarbon comprises $C_{3-}$ olefin and (ii) the $C_{3-}$olefin comprises primarily ethylene+propylene that is ≥10.0 wt. % (ethylene+propylene), based on the weight of the first hydrocarbon's $C_{3-}$ olefin, e.g., ≥50.0 wt. %, such as ≥75.0 wt. %, or ≥95.0 wt. % (ethylene+propylene). Optionally, the first hydrocarbon comprises ≥50.0 wt. % of $C_{3-}$ olefin, based on the weight of the first hydrocarbon, e.g., ≥75.0 wt. %, such as ≥90.0 wt. %. Optionally, the first hydrocarbon comprises ≥50.0 wt. % of propylene, based on the weight of the first hydrocarbon, e.g., ≥75.0 wt. %, such as ≥90.0 wt. %. Optionally, the first hydrocarbon has a propylene:ethylene weight ratio $PE_1 \geq 10.0$, e.g., ≥$1.0 \times 10^2$, such as ≥$1.0 \times 10^3$. In certain aspects, the first hydrocarbon contains substantially no ethylene, e.g., ≤0.1 wt. % of ethylene based on the weight of the first product. The first hydrocarbon can further comprise (i) $C_{5+}$ hydrocarbon, e.g., 5.0 wt. % to 50 wt. % of $C_{5+}$ hydrocarbon, such as 10.0 wt. % to 30.0 wt. %, and/or (ii) $C_{4-}$ saturated hydrocarbon, e.g., 1.0 wt. % to 20.0 wt. % of $C_{4-}$ saturated hydrocarbon, such as 5.0 wt. % to 15.0 wt. %, the weight percents being based on the weight of the first hydrocarbon. The first hydrocarbon can further comprise $C_4$ olefin.

The first oxygenate is primarily water, e.g., ≥50.0 wt. % water based on the weight of the first oxygenate, such as ≥90.0 wt. %. The first hydrocarbon and first oxygenate can be conducted away from the second stage as components of a second product mixture.

At least part of the first stream's methanol is reacted in a first stage to produce a first hydrocarbon and first oxygenate, e.g., ≥50.0 wt. %, such as ≥75.0 wt. % or ≥90.0 wt. % based on the weight of methanol in the first stream. The first hydrocarbon generally comprises $C_{3-}$ olefin, the $C_{3-}$ olefin comprising ≥25.0 wt. % of propylene and ≤10.0 wt. % of ethylene, based on the weight of the first hydrocarbon's $C_{3-}$ olefin.

In certain aspects, the first stage includes reacting the at least a portion (e.g., ≥50.0 wt. %, such as ≥75.0 wt. %, or ≥90.0 wt. %) of the first stream's methanol (generally at least a portion of which is in the vapor phase) over a first catalyst, such as alumina, to obtain a first vapor mixture containing dimethyl ether ("DME"). The DME-containing first vapor mixture is then reacted over a shape-selective molecular sieve catalyst disposed in at least two series-connected tubular reactors to produce a product mixture containing propylene. Suitable shape-selective molecular sieves comprise aluminosilicate zeolites having a Constraint Index of 1 to 12. Constraint Index is defined in U.S. Pat. No. 4,016,218 and suitable aluminosilicate zeolites with a Constraint Index of 1 to 12 include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. In one preferred embodiment, the molecular sieve is ZSM-5 with an alkali content of less than 380 ppm and preferably less than 200 ppm, a ZnO content of less than 0.1 wt-%, a CdO content of less than 0.1 wt. %, a BET surface area of 300 to 600 $m^2/g$, and a pore volume (determined by mercury porosimetry) of 0.3 to 0.8 $m^3/g$.

Suitable conditions for the first stage conversion of methanol to DME include a temperature in the range of from 200° C. to 350° C., a pressure in the range of from 100 kPa to 1000 kPa, and a methanol weight hourly space velocity from 1 $hr^{-1}$ to 6 $hr^{-1}$. Suitable conditions for the second stage conversion of DME to propylene include a temperature in the range of from 350° C. to 500° C., a pressure in the range of from 100 kPa to 1000 kPa and a DME weight hourly space velocity in the range of from 1 $hr^{-1}$ to 5 $hr^{-1}$. Under these conditions, ≥10.0 wt. % of the first stream's methanol is converted to propylene, based on the weight of the first stream's methanol, e.g., ≥20.0 wt. %, such as ≥30.0 wt. %. Further details of this methanol to propylene conversion process can be found in the Handbook of Petroleum Production Processes, Chapter 10.1, McGraw-Hill, 2005, and in U.S. Pat. No. 7,015,369, the entire contents of both being incorporated herein by reference. A first product mixture can be conducted away from the first stage, the first product mixture comprising (i) at least a portion of the propylene produced in the first stage by reacting the first stream's methanol and optionally (ii) at least a portion of any by-products, such as at least a portion of any water, $C_{5+}$ hydrocarbon, and/or $C_{4-}$ saturated hydrocarbon. In certain aspects, the product mixture discharged from the last tubular reactor in this process has a propylene content of 20 to 50 vol. % based on the total volume of the first product mixture.

In certain aspects, the first product mixture comprises ≥10.0 wt. % propylene, e.g., ≥20.0 wt. %, such as ≥30.0 wt. %; ≥1.0 wt. % of $C_{5+}$ hydrocarbon, e.g., ≥2.0 wt. %, such as ≥3.0 wt. %; ≥0.01 wt. % of $C_{4-}$ saturated hydrocarbon, e.g., ≥0.02 wt. %, such as ≥0.03 wt. %; and ≥30.0 wt. % water, e.g., ≥40.0 wt. %, such as ≥50.0 wt. %; the weight percents being based on based on the weight of the first product mixture. Generally, the first product mixture comprises ≤15.0 wt. % of $C_{5+}$ hydrocarbon, e.g., ≤10.0 wt. %, such as ≤5.0 wt. %; and ≤0.15 wt. % of $C_{4-}$ saturated hydrocarbon, e.g., ≤0.10 wt. %, such as ≤0.05 wt. %. The first product mixture can contain small amounts of other by-products, e.g., ethylene, $C_4$ olefin, and/or oxygenate. When present, the amount of such by-products is generally ≤1.0 wt. %, e.g., ≤0.1 wt. %, such as ≤0.01 wt. %, based on the weight of the first product mixture. The weight fraction of the first product mixture that is propylene (weight of propylene in the product mixture divided by the weight of the product mixture) has the value $P_1$. $P_1$ is generally ≥0.1, e.g., ≥0.2, such as ≥0.3.

Conventional separation means can be utilized for separating propylene from the first product mixture, but the invention is not limited thereto. Suitable separation means are disclosed in U.S. Patent Application Publication No. 2008/0033218 A1.

In certain aspects, at least a portion of the first product mixture is conducted to a second separation stage for removing propylene from the first product mixture. The second separation stage can include one or more of the separation means disclosed in U.S. Patent Application Publication No. 2008/0033218 A1, for example. In other aspects, at least a portion of the first product mixture is conducted to the first separation stage, e.g., by combining at least a portion of the first product mixture with at least a portion of the alcohol-containing mixture, or one or more components thereof The combining can be carried out in the first separation stage, and/or at a location upstream thereof These aspects of the invention are efficient because, e.g., water present in the first product mixture can be removed using the water-removal means present in the first separation stage for removing water from the alcohol-synthesis process effluent, obviating the need for additional water-removal means in a second separation stage. For greater efficiency, propylene-removal means can be located in the first separation stage for removing propylene from the first product mixture. Other by-products (non-aqueous, and especially non-water by-products) in the first product mixture can be removed in the first separation stage. For example, the first separation stage can contain additional separation means for removing at least a portion of any $C_{5+}$ hydrocarbon, $C_2$ olefin, $C_4$ olefin, and/or $C_{4-}$ saturated hydrocarbon that might be present in the first product mixture. Separated propylene can be conducted away from the process, e.g., for storage or further processing, including polymerization.

Reacting the Second Stream

At least a portion of the $C_{2+}$ alcohol in the second stream are reacted in a second stage to convert at least a portion of the second stream's $C_{2+}$ alcohol to olefins, e.g., ethylene and propylene. For example, ≥50.0 wt. % of the second stream's $C_{2+}$ alcohol, based on the weight of the second stream's $C_{2+}$ alcohol, ≥75.0 wt. %, such as ≥90.0 wt. %, or ≥95.0 wt. % can be reacted in a second stage to produce a second hydrocarbon and a second oxygenate, wherein (i) the second hydrocarbon comprises $C_{2+}$ olefin and (ii) the $C_{2+}$ olefin comprises a total amount of ethylene+propylene that is ≥10.0 wt. %, based on the weight of the second hydrocarbon's $C_{2+}$ olefin. The second hydrocarbon optionally comprises ≥50.0 wt. % of $C_{2+}$ olefin, based on the weight of the second hydrocarbon, e.g., ≥75.0 wt. %, such as ≥90.0 wt. %. Optionally, the $C_{2+}$ olefin comprises primarily ethylene and propylene, e.g., ≥50.0 wt. % of ethylene+propylene, based on the weight of the second hydrocarbon, such as ≥75.0 wt. %, or ≥90.0 wt. %. Optionally, the second hydrocarbon has a propylene:ethylene weight ratio $PE_2$ ≥0.10, e.g., ≥0.20, such as ≥0.30, or ≥0.40, or ≥0.50. For example, the second hydrocarbon can have a propylene:ethylene weight ratio in the range of from 0.10 to 0.60, e.g., about 0.20 to about 0.50, or about 0.30 to about 0.40. The second oxygenate is primarily water, e.g., ≥50.0 wt. % water based on the weight of the second oxygenate. The second hydrocarbon and second oxygenate can be conducted away from the second stage as components of a second product mixture.

In certain aspects, the second stage includes at least one conventional alcohol dehydrogenation reaction, where the $C_{2+}$ alcohols in the second stream are converted to their corresponding olefins by dehydration. In these aspects, the dehydration can be, e.g., conducted in the presence of a solid acid catalyst, such as amorphous and/or crystalline $Al_2O_3$, $ZrO_2$, and/or $WO_3$, either alone or supported on metal oxides and sulfides of W, V, Zr, and/or Mo. Polyoxometalates containing W and/or Mo are also suitable dehydration catalysts. Suitable conditions for the dehydration reaction include a temperature of at least 180° C., such as in the range of from 180° C. to 450° C. and a pressure in the range of from 0.5 atm to about 25 atm absolute (from 50 kPa to 2.5 MPa). Suitable conventional alcohol dehydrogenation processes include those described in U.S. Pat. Nos. 4,062,905; 4,079,095; 4,079,096; 3,911,041; and 4,049,573, each of which is incorporated by reference herein in its entirety.

In aspects where the second stage includes at least one conventional alcohol dehydrogenation reaction, the second product mixture generally comprises propylene and ethylene, the propylene and ethylene being present in a propylene:ethylene weight ratio that is substantially equal to the second stream's propanol:ethanol weight ratio. The term "substantially" equal in this case means within about +/−10% of equal, such as within about +/−5% of equal. For example, when the second stream has an propanol: ethanol weight ratio in the range of from 0.01 to 1.0, e.g., 0.05 to 0.70, such as 0.10 to 0.50, the second product mixture's propylene: ethylene weight ratio is substantially within the range of from 0.01 to 1.0, e.g., substantially in the range of 0.05 to 0.70, such as substantially in the range of 0.10 to 0.50. In certain aspects where the second stage includes conventional alcohol dehydrogenation, the second product mixture comprises ≥20.0 wt. % ethylene, e.g., ≥30.0 wt. %, such as ≥40.0 wt. %; ≥10.0 wt. % propylene, e.g., ≥20.0 wt. %, such as ≥30.0 wt. %; ≤1.0 wt. % of $C_{5+}$ hydrocarbon, e.g., ≤0.1 wt. %, such as ≤0.01 wt. %; ≤1.0 wt. % of $C_{4-}$ saturated hydrocarbon, e.g., ≤0.1 wt. %, such as ≤0.01 wt. %; and ≥30.0 wt. % water, e.g., ≥40.0 wt. %, such as ≥50.0 wt. %; the weight percents being based on based on the weight of the second product mixture. The second product mixture can contain small amounts of other by-products, e.g., $C_4$ olefin, and/or oxygenate such as one or more ethers. When present, the amount of such by-products is generally ≤1.0 wt. %, e.g., ≤0.1 wt. %, such as ≤0.01 wt. %, based on the weight of the second product mixture. The weight fraction of the second product mixture that is propylene (weight of propylene in the second product mixture divided by the weight of the second product mixture) has the value $P_2$. $P_2$ is generally ≥0.1, e.g., ≥0.2, such as ≥0.3. The weight fraction of the second product mixture that is ethylene (weight of ethylene in the second product mixture divided by the weight of the second product mixture) has the value $E_2$. $E_2$ is generally ≥0.2, e.g., ≥0.3, such as ≥0.4.

In certain aspects, the second stage includes at least one alcohol conversion reaction, where the $C_{2+}$ alcohols in the second stream are converted to olefins in at least one oxygenate-to-olefin ("OTO") reaction carried out in the presence of at least one aluminophosphate molecular sieve OTO catalyst. Suitable OTO reactions include those described in U.S. Pat. Nos. 4,499,327 and 6,518,475, both of which are incorporated by reference herein in their entirety. OTO reactions differ from conventional alcohol dehydrogenation reactions. One difference is found in the relationship between (i) the weight ratios of component alcohols in the olefin-synthesis reaction's feed and (ii) the weight ratios of the equivalent olefins in the reaction product. These ratios are strongly correlated in conventional alcohol dehydrogenation, with, e.g., the $C_2$ alcohol: $C_3$ alcohol weight ratio in the olefin synthesis reaction's feed being substantially the same as the $C_2$ olefin:$C_3$ olefin weight ratio in the olefin synthesis reaction's product. In OTO reactions, the weight ratios of olefins in the product generally do not correlate strongly with the weight ratios of the equivalent alcohols in the feed.

This effect is observed in U.S. Patent Application Publication No. 2007/0259972 A1, which discloses that an OTO reaction converts ethanol to primarily ethylene, methanol converts to generally equal amounts of ethylene and propylene. This would lead one skilled in the art to expect that an OTO reaction would convert propanol to primarily propylene. This has been found to not be the case. Contrary to expectations, when one or more OTO processes (such as those disclosed in U.S. Patent Application Publication No. 2007/0259972A1) are utilized for reacting the second stream, increasing the amount of $C_3$ alcohol in the second stream leads to an increase in ethylene produced in the OTO reaction.

Certain aspects of the invention utilize a second stage which includes one or more of the OTO reactions described in U.S. Patent Application Publication Nos. 2007/0259972A1, 2008/0033218A1, and 2005/0107481A1. An important difference between those OTO processes and OTO processes utilized in aspects of the second stage of this invention, is that the conventional OTO processes do not separate from mixed alcohols (i) a methanol-containing stream and (ii) a $C_{2+}$ alcohol-containing stream, and then separately process streams (i) and (ii) in order to produce primarily propylene (from stream (i)) and primarily ethylene (from stream (ii)). Instead, the conventional process transfers to an OTO reaction mixed alcohols, such as mixed alcohols containing, e.g., at least 40 wt. % methanol and at least 3 wt. % ethanol, and at least 1 wt. % propanol (per U.S. Patent Application Publication No. 2008/0033218A1).

In aspects where the second stage includes at least one OTO reaction, the second product mixture generally comprises propylene and ethylene, the propylene and ethylene being present in a propylene:ethylene weight ratio that is not well-correlated with the second stream's propanol:ethanol weight ratio. The term "not well correlated" in this case means that the propylene:ethylene weight ratio differs from the second stream's propanol:ethanol weight ratio by more than about +/−10% of equal, such as more than about 15%, or more than about 20%.

In certain aspects where the second stage includes at least one OTO reaction, the second product mixture comprises ≥20.0 wt. % ethylene, e.g., ≥30.0 wt. %, such as ≥40.0 wt. %; ≥5.0 wt. % propylene, e.g., ≥10.0 wt. %, such as ≥15.0 wt. %; ≤1.0 wt. % of $C_{5+}$ hydrocarbon, e.g., ≤0.1 wt. %, such as ≤0.01 wt. %; ≤1.0 wt. % of $C_{4-}$ saturated hydrocarbon, e.g., ≤0.1 wt. %, such as ≤0.01 wt. %; and ≥30.0 wt. % water, e.g., ≥40.0 wt. %, such as ≥50.0 wt. %; the weight percents being based on based on the weight of the second product mixture. The second product mixture can contain small amounts of other by-products, e.g., $C_4$ olefin, and/or oxygenate such as one or more ethers. When present, the amount of such by-products is generally ≤1.0 wt. %, e.g., ≤0.1 wt. %, such as ≤0.01 wt. %, based on the weight of the second product mixture. The weight fraction of the second product mixture that is propylene (weight of propylene in the second product mixture divided by the weight of the second product mixture) has the value $P_2$. $P_2$ is generally ≥0.05, e.g., ≥0.1, such as ≥0.15. The weight fraction of the second product mixture that is ethylene (weight of ethylene in the second product mixture divided by the weight of the second product mixture) has the value $E_2$. $E_2$ is generally ≥0.2, e.g., ≥0.3, such as ≥0.4.

In certain aspects, (i) the first stream contains substantially all of the alcohol-containing mixture's methanol, (ii) the second stream contains substantially all of the alcohol-containing stream's $C_2$-$C_4$ alcohol, and (iii) the alcohol-containing stream has a methanol: $C_2$-$C_4$ alcohol weight ratio in the range of about 0.1 to about 4.0, e.g., about 0.33 to about 0.30. In related aspects, when (i) the alcohol-containing mixture has a molar ratio of methanol to $C_{3-}$ alcohol in the range of from 1.0 to 4.0, e.g., in the range of from 1.5 to 3.0; (ii) the first stream contains substantially all of the alcohol-containing mixture's methanol; (iii) the second stream contains substantially all of the alcohol-containing stream's $C_{3-}$ alcohol; and (iv) the total olefin product of the process (first and second stage) has a propylene:ethylene weight ratio that is ≥1.0, e.g., ≥1.1, such as ≥1.25, or ≥1.5, or ≥2.0, including in the range of from about 1.1 to about 4.0, such as about 1.25 to 2.0. When the specified first stage is utilized for converting the first stream and an OTO reaction is utilized in the second stage for reacting the second stream, these first and second streams together have a propylene:ethylene weight ratio ≥1.0, or ≥1.1, or ≥1.2, or ≥1.5, or ≥2.0, e.g., in the range of 1.1 to 2.5, such as in the range of 1.25 to 2.0. For example, the first and second hydrocarbons together can have a propylene:ethylene weight ratio $P_3$ that is ≥1.0, or ≥1.1, or ≥1.2, or ≥1.5, or ≥2.0, e.g., in the range of 1.1 to 2.5, such as in the range of 1.25 to 2.0. The same result can be achieved when conventional alcohol dehydration is substituted for OTO in the second stage, provided the amounts of ethanol and propanol in the second stream (and alcohol-containing mixture) are selected to produce the designated amounts of the corresponding olefins in the second product mixture.

Conventional separation means can be utilized for separating olefins, e.g., ethylene and/or propylene from the second product mixture, but the invention is not limited thereto. Suitable separation means are disclosed in U.S. Patent Application Publication No. 2008/0033218 A1.

In certain aspects, at least a portion of the second product mixture is conducted to a third separation stage for removing ethylene and/or propylene from the second product mixture. The third separation stage generally includes means for separating ethylene, e.g., one or more cryogenic ethylene separators, and can further include one or more of the separation means disclosed in connection with the second separation stage. In other aspects, at least a portion of the second product mixture is conducted to the first separation stage, e.g., by combining at least a portion of the second product mixture with at least a portion of the alcohol-containing mixture, the first product mixture (when at least a portion thereof is conducted to the first separation stage), or one or more components thereof. The combining can be carried out in the first separation stage and/or at a location upstream thereof. These aspects of the invention are efficient for many of the same reasons as in the case of the first product stream. For greater efficiency, ethylene and/or propylene-removal means can be located in the first separation stage for removing propylene from the first and/or second product mixtures. Other by-products (non-aqueous, and especially non-water by-products) in the second product mixture can be removed in the first separation stage. Separated light olefin, e.g., separated ethylene and/or propylene can be conducted away from the process, e.g., for storage or further processing, including polymerization. The $C_{2+}$ olefin produced by the present process can be used as feedstocks in a variety of important industrial processes, including the production of homopolymers and copolymers of ethylene and propylene.

Combined First and Second Product Mixtures

Although individual olefin-containing streams, such as an ethylene-containing stream and a propylene-containing stream, can be conducted away from the process. In other aspects, at least one olefin-containing stream containing a plurality of $C_{2+}$ olefins is conducted away from the process. For example, at least a portion of the first product mixture (or one or more components thereof, such as at least a portion of the first product mixture's propylene) can be combined with at least a portion of the second product mixture (or one or more components thereof, such as at least a portion of the second product mixture's ethylene and/or at least a portion of the second product mixture's propylene). The combining can be carried out, e.g., by physically mixing the first product mixture and the second product mixture. This can be done, e.g., downstream of the first and second stages, such as by combining the first and second product mixtures in the first separation stage (in aspects where those product streams are conducted to first separation stage) and/or downstream of the second and third separation stages. In certain aspects, the combined product mixture (i) contains substantially all of the $C_{3-}$ olefin produced in the first and second stages and (ii) has a propylene:ethylene weight ratio ≥1.0, e.g., in the range of 1.1 to 2.5, such as in the range of 1.25 to 2.0.

Regulating the Propylene: Ethylene Weight Ratio

Certain aspects of the invention include regulating the weight ratio of the ethylene and propylene produced in the first and second stage by adjusting at least one of (i) the amount of first stream conducted to the first stage, (ii) the amount of second stream conducted to the second stage, (iii) the relative amount of methanol the first stream, and (iv) the relative amount of $C_{2+}$ alcohol in the second stream. The process can be operated in a "closed loop", e.g., by measuring the combined product mixture's propylene: ethylene ratio, generating a differential by subtracting the desired propylene: ethylene weight ratio from the measured propylene: ethylene weight ratio, and then utilizing the differential to calculate the amount of adjustment needed in one or more of (i) to (iv), in order to substantially minimize the differential. Computing means, such as one or more digital and/or analog computers can be utilized for the calculating.

Although the effect is believed to be smaller, related aspects of the invention include adjusting the amount of $C_3$ alcohol in the second stream. For example, the amount of $C_3$ alcohol in the second stream can be set to a designated value in the range of 0.1 wt. % to 2.0 wt. % in order to trim the combined product mixture's propylene: ethylene weight ratio to a designated value in the range of from 1.1 to 2.5. The amount of $C_3$ alcohol in the second stream can be adjusted by any convenient method, including conventional methods such as one or more of (i) regulating source material composition, (ii) regulating process conditions during the reacting of the source material to produce an alcohol-containing mixture having the desired amount of $C_3$ alcohol, (iii) separating and conducting away excess $C_3$ alcohol from the alcohol-containing mixture, etc. The process can be operated in a "closed loop" using, e.g., substantially the same methods utilized for adjusting the amount of first stream conducted to the first stage.

In certain aspects, the alcohol-containing mixture further comprises water. Optionally, (particularly in embodiments where one or more OTO reactions are utilized for reacting the second stream), at least a portion of the alcohol-containing mixture's water is present in the second stream. The amount of water in the second stream can be utilized for regulating the selectivity of the OTO process toward ethylene and/or propylene, e.g., to trim the propylene: ethylene weight ratio in the combined product mixture to a designated value. This can be accomplished utilizing substantially the same methods as those utilized for adjusting the amount of first stream conducted to the first stage.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of," or "is" preceding the recitation of the composition, component, or components, and vice versa.

The invention claimed is:

1. A process for producing one or more $C_{2+}$ olefins, the process comprising:
   (a) providing an alcohol-containing mixture comprising $C_{2+}$ alcohols and ≥2 wt. % of methanol, wherein the $C_{2+}$ alcohols include at least ethanol and propanol and wherein the alcohol-containing mixture comprises ≥15 wt. % of ethanol, the weight percentages being based on the weight of the alcohol-containing mixture;
   (b) separating a first stream and a second stream from the alcohol-containing mixture, wherein (i) the first stream comprises ≥90.0 wt. % of the alcohol-containing mixture's methanol based on the weight of the alcohol-containing mixture's methanol, (ii) the second stream comprises ≥90.0 wt. % of the alcohol-containing mixture's $C_{2+}$ alcohols, based on the weight of the alcohol-containing mixture's $C_{2+}$ alcohols, and (iii) the second stream has a propanol: ethanol weight ratio in the range of from 0.10 to 0.50;
   (c) reacting at least part of the first stream's methanol to produce a first hydrocarbon and a first oxygenate, the first hydrocarbon comprising ≥25.0 wt. % of propylene and ≤10.0 wt. % of ethylene, the weight percentages being based on the weight of the first hydrocarbon, wherein the first hydrocarbon has a first propylene: ethylene weight ratio $P_1$ that is ≥10.0; and
   (d) reacting in at least one oxygenate to olefin reactor at least part of the second stream's $C_{2+}$ alcohols to produce a second product comprising a second hydrocarbon and a second oxygenate, wherein (i) the second hydrocarbon comprises one or more $C_{2+}$ olefins, (ii) the second product comprises ≥20.0 wt. % ethylene, based on the weight of the second product, (iii) the second hydrocarbon has a second propylene:ethylene weight ratio $P_2$ in the range of 0.30 to 0.40, and (iv) the first hydrocarbon and the second hydrocarbon together have a propylene: ethylene weight ratio $P_3$ in the range of from 1.1 to 2.5.

2. The process of claim 1, wherein the process further comprises producing the alcohol-containing mixture by:
   (e) providing a feed mixture, the feed mixture comprising molecular hydrogen and ≥5.0 wt. % of carbon monoxide, based a the weight of the feed mixture, the feed mixture having a $H_2:(CO+CO_2)$ molar ratio in the range of from 0.5 to 20; and
   (f) reacting at least a portion of the feed mixture's molecular hydrogen with at least a portion of the feed mixture's carbon monoxide, the reacting being carried out in the presence of a catalyst comprising one or more elements or oxides thereof from Groups 8 to 12 of the Periodic Table to produce the alcohol-containing mixture, wherein (i) the molar ratio of methanol to $C_{2+}$ alcohols in the alcohol-containing mixture is in the range of from 1.5:1 to 3:1 and (ii) the alcohol-containing mixture comprises ≥10 wt. % of methanol, the weight percentage being based on the weight of the alcohol-containing mixture.

3. The process of claim 1, wherein the alcohol-containing mixture comprises ≥50.0 wt. % $C_{3-}$ alcohols based on the weight of the alcohol-containing mixture.

4. The process of claim 2, wherein the catalyst comprises CuO and ZnO supported on alumina and promoted with caesium or a compound thereof.

5. The process of claim 1, wherein the alcohol-containing mixture comprises at least 15 wt. % methanol.

6. The process of claim 1, wherein the reacting (c) comprises reacting at least part of the methanol in the first stream in the presence of a molecular sieve catalyst.

7. The process of claim 6, wherein the molecular sieve catalyst comprises ZSM-5.

8. The process of claim 1, further comprising polymerizing at least a portion of (i) the first hydrocarbon's propylene and/or ethylene and/or (ii) the second hydrocarbon's ethylene and/or propylene.

9. The process of claim 1, wherein the second product comprises ≥30.0 wt. % ethylene, based on the weight of the second product; or wherein the second product comprises ≥10.0 wt. % propylene, based on the weight of the second product; or a combination thereof.

10. A process for producing ethylene and propylene, comprising:
   (a) providing a source material comprising at least 10 vol. % of at least one hydrocarbon;
   (b) reacting at least a portion of the source material's hydrocarbon to produce a feed mixture, the feed mixture comprising molecular hydrogen and ≥5.0 wt. % of carbon monoxide, the weight percentage being based on the weight of the feed mixture, the feed mixture having an $H_2:(CO+CO_2)$ molar ratio in the range of from 0.5 to 20;

(c) reacting at least a portion of the feed mixture's molecular hydrogen with at least a portion of the feed mixture's carbon monoxide, the reacting being carried out in the presence of a catalyst comprising one or more elements or oxides thereof from Groups 8 to 12 of the Periodic Table, to produce an alcohol-containing mixture comprising methanol and $C_{2+}$ alcohols, wherein the $C_{2+}$ alcohols include at least ethanol and propanol and wherein the alcohol-containing mixture comprises ≥10 wt. % of ethanol based on the weight of the alcohol-containing mixture, and wherein the molar ratio of methanol to $C_{2+}$ alcohols in the alcohol-containing mixture is in the range of from 1.5:1 to 3:1;

(d) separating a first stream and a second stream from the alcohol-containing mixture, wherein (i) the first stream comprises ≥90.0 wt. % of the alcohol-containing mixture's methanol based on the weight of the alcohol-containing mixture's methanol, (ii) the second stream comprises ≥90.0 wt. % of the alcohol-containing mixture's $C_{2+}$ alcohols, based on the weight of the alcohol-containing mixture's $C_{2+}$ alcohols, and (iii) the second stream has a propanol: ethanol weight ratio in the range of from 0.10 to 0.50;

(e) reacting at least part of the first stream's methanol to produce a first hydrocarbon and a first oxygenate, wherein (i) the first hydrocarbon comprises $C_{3-}$ olefins and (ii) the $C_{3-}$ olefins comprise ≥25.0 wt. % of propylene and ≤10.0 wt. % of ethylene, based on the weight of the first hydrocarbon's $C_{3-}$ olefins, and (iii) the first hydrocarbon has a first propylene:ethylene weight ratio that is ≥10.0; and (f) reacting in at least one oxygenate to olefin reactor at least part of the second stream's $C_{2+}$ alcohols to produce a second product comprising a second hydrocarbon and a second oxygenate, wherein (i) the second hydrocarbon comprises $C_{2+}$ olefins, (ii) the second product comprises ≥20.0 wt. % ethylene, based on the weight of the second product, (iii) the second hydrocarbon has a second propylene:ethylene weight ratio $P_2$ in the range of from 0.30 to 0.40, and (iv) the first hydrocarbon and the second hydrocarbon together have a propylene:ethylene weight ratio $P_3$ in the range of from 1.1 to 2.5.

11. The process of claim 10, wherein the source material comprises ≥50 vol. % methane, based on the volume of the source material.

12. The process of claim 10, wherein the amount of $C_{3-}$ olefins in the first hydrocarbon is ≥50.0 wt. %, based on the weight of the first hydrocarbon, and wherein the amount of $C_{2+}$ olefins in the second hydrocarbon is ≥50.0 wt. %, based on the weight of the second hydrocarbon.

13. The process of claim 10, wherein the alcohol-containing mixture comprises at least 15 wt. % methanol.

14. The process of claim 10, wherein the alcohol-containing mixture further comprises one or more of carbon monoxide or molecular hydrogen, and further comprising recycling from the alcohol-containing mixture to the feed mixture said one or more of carbon monoxide or molecular hydrogen.

15. The process of claim 10, wherein step (d) further comprises separating a third stream, a fourth stream, and a fifth stream from the alcohol-containing mixture, wherein the third stream comprises $C_{5+}$ hydrocarbons, the fourth stream comprises acetaldehyde, and the fifth stream comprises water.

16. The process of claim 10, further comprising recovering a first product mixture, the first product mixture comprising the first hydrocarbon and the first oxygenate produced in step (e).

17. The process of claim 16, wherein the first oxygenate comprises ≥90.0 wt. % water, based on the weight of the first oxygenate, and wherein the first product mixture further comprises $C_{5+}$ hydrocarbons and saturated $C_{4-}$ hydrocarbons.

18. The process of claim 16, further comprising recovering a second product mixture, the second product mixture comprising the second hydrocarbon and the second oxygenate produced in step (f).

19. The process of claim 10, wherein the second oxygenate comprises ≥90.0 wt. % water, based on the weight of the second oxygenate.

20. The process of claim 10, wherein the second product comprises ≥30.0 wt. % ethylene, based on the weight of the second product; or wherein the second product comprises ≥10.0 wt. % propylene, based on the weight of the second product; or a combination thereof.

* * * * *